(12) United States Patent
El Zoghbi

(10) Patent No.: US 11,105,613 B2
(45) Date of Patent: Aug. 31, 2021

(54) UNIVERSAL DIRECT MEASUREMENT DEPTH GAUGE

(71) Applicant: DePuy Synthes Products, Inc., Raynham, MA (US)

(72) Inventor: Gaser El Zoghbi, Solothurn (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 181 days.

(21) Appl. No.: 16/037,128

(22) Filed: Jul. 17, 2018

(65) Prior Publication Data

US 2019/0041195 A1 Feb. 7, 2019

Related U.S. Application Data

(60) Provisional application No. 62/541,832, filed on Aug. 7, 2017.

(51) Int. Cl.
*G01B 11/22* (2006.01)
*B23Q 17/09* (2006.01)
(Continued)

(52) U.S. Cl.
CPC .......... *G01B 11/22* (2013.01); *A61B 17/1626* (2013.01); *A61B 90/03* (2016.02);
(Continued)

(58) Field of Classification Search
CPC ... G01B 11/22; G01B 11/043; A61B 17/1613; A61B 17/16; A61B 17/1626; A61B 90/06; A61B 2090/062; A61B 90/03; A61B 17/1707; B23B 49/00; B23B 49/003; B23B 49/02; B23B 2260/0485; B25D 2250/055;
(Continued)

(56) References Cited

U.S. PATENT DOCUMENTS 5,404,021 A 4/1995 Mangano et al.
6,587,184 B2 7/2003 Würsch et al.
(Continued)

FOREIGN PATENT DOCUMENTS

DE 2838968 C2 6/1984
WO 2016/049467 A1 3/2016

OTHER PUBLICATIONS

International Patent Application No. PCT/IB2018/055825: International Search Report and Written Opinion dated Oct. 30, 2018, 13 pages.

*Primary Examiner* — Marcela I. Shirsat
(74) *Attorney, Agent, or Firm* — Kramer Amado PC

(57) ABSTRACT

A depth gauge device including a body extending a central longitudinal axis and including a channel and a light-passing hole, the light passing hole open to the channel, a light source mounted in the body for generating a light beam, the light beam passing through the light-passing hole toward a surface of a drill-bit extending through the channel, the light beam forming an incident light beam when reflected away from the drill-bit surface, an image sensor mounted in the body for sensing the incident light beam and generating a plurality of successive images of the drill-bit surface to detect variations in the position of the drill-bit moving through the channel and an clamp coupled to the body, the clamp including a plurality of adjustable arms configured to clamp the device to a protection sleeve.

16 Claims, 4 Drawing Sheets

(51) Int. Cl.
*B23B 49/00* (2006.01)
*A61B 90/00* (2016.01)
*G01B 11/04* (2006.01)
*A61B 17/16* (2006.01)
*A61B 17/17* (2006.01)

(52) U.S. Cl.
CPC .............. *A61B 90/06* (2016.02); *B23B 49/00* (2013.01); *B23Q 17/0923* (2013.01); *G01B 11/043* (2013.01); *A61B 17/1707* (2013.01); *A61B 2090/062* (2016.02); *B23B 49/003* (2013.01); *B23B 2260/0485* (2013.01); *B25D 2250/055* (2013.01); *Y10T 408/8925* (2015.01)

(58) Field of Classification Search
CPC .............. Y10T 408/8925; Y10T 408/97; Y10T 408/99
USPC ......................................................... 606/102
See application file for complete search history.

(56) References Cited

U.S. PATENT DOCUMENTS

| | | | |
|---|---|---|---|
| 6,681,869 B2 | 1/2004 | Würsch et al. | |
| 6,786,683 B2 | 9/2004 | Schaer et al. | |
| 7,513,722 B2 * | 4/2009 | Greenberg | B23B 49/005 |
| | | | 408/202 |
| 7,740,425 B2 * | 6/2010 | Zeiler | B23B 49/006 |
| | | | 408/9 |
| 8,092,457 B2 * | 1/2012 | Oettinger | A61B 17/1626 |
| | | | 600/547 |
| 9,204,885 B2 | 12/2015 | McGinley et al. | |
| 2003/0208103 A1 * | 11/2003 | Sonnenschein | A61M 16/0493 |
| | | | 600/117 |
| 2005/0222520 A1 * | 10/2005 | Faciszewski | A61B 10/0266 |
| | | | 600/564 |
| 2006/0241628 A1 | 10/2006 | Parak | |
| 2014/0329197 A1 | 11/2014 | Bassett et al. | |
| 2017/0296204 A1 * | 10/2017 | Matsuura | A61B 17/1707 |

* cited by examiner

UNIVERSAL DIRECT MEASUREMENT DEPTH GAUGE

CROSS REFERENCE TO RELATED APPLICATIONS

This present application claims priority to U.S. Provisional Patent Application Ser. No. 62/541,832 filed on Aug. 7, 2017 the entire disclosure is expressly incorporated herein by reference.

BACKGROUND

It is often necessary to exactly assess the depth of a hole drilled within bone, for example, to determine the required length of a bone screw. Trauma implants today use multiple measuring devices to determine the length of a screw necessary to fit within a drilled hole. These measuring devices vary dependent on the implant and the anatomical region, requiring multiple different measuring devices to fit to different drill bits. Furthermore, many of the current measuring devices employing mechanical, electromechanical, and/or electrical/electronic techniques for sensing or determining relative distances may be inaccurate, resulting in the selection of screws of the wrong length. Using a screw that is too long may increase the risk of soft tissue irritation while using a screw that is too short may risk the loss of primary stability. Thus, there is need for a new depth-measuring instrument that is compatible with a variety of drill bits and provides a fast and accurate measurement.

SUMMARY

The present disclosure relates to a depth gauge device, comprising a body extending a central longitudinal axis and including a channel and a light-passing hole, the light passing hole open to the channel, a light source mounted in the body for generating a first light beam, the first light beam passing through the light-passing hole toward a surface of a drill-bit extending through the channel, the first light beam forming an incident light beam when reflected away from the drill-bit surface, an image sensor mounted in the body for sensing the incident light beam and generating a plurality of successive images of the drill-bit surface to detect variations in the position of the drill-bit moving through the channel and a clamp coupled to the body, the clamp including a plurality of adjustable arms configured to clamp the device to a protection sleeve. In an embodiment, the clamp further comprises a rotatable clamp adjustment mechanism, wherein rotating the adjustment mechanism in a first direction moves the plurality of arms toward the central longitudinal axis and rotating the adjustment mechanism in a second direction moves the plurality of arms away from the central longitudinal axis. In another embodiment, the device includes a processing unit coupled to the image sensor, the processing unit comparing the movement of identifiable points within the plurality of successive images to calculate the distance the drill-bit moves through the channel. In an embodiment, the light source is an infrared laser source. In a further embodiment, the light-passing hole is sized and shaped for the passing of the first light beam from the light source and the incident light beam reflected from the drill-bit surface. In another embodiment, the device further comprises a display screen coupled to the processing unit, the display screen displaying the distance the drill-bit moves through the channel. In a further embodiment, the processing unit includes Bluetooth capabilities. In another embodiment, the device is clamped to the protection sleeve, the channel is aligned with a channel extending through the protection sleeve.

The present disclosure also relates to a system for measuring the depth of a hole comprising a depth gauge having a depth gauge channel extending therethrough, the depth gauge including a laser source disposed therein for emitting a laser light beam toward a target drill-bit surface within the depth gauge channel and a light sensor for sensing an incident laser beam reflected from the drill-bit surface, a protection sleeve coupled to the depth gauge, the protection sleeve including a protection sleeve channel aligned with the depth gauge channel when the protection sleeve is coupled to the depth gauge, and a drill-bit configured to extend into the depth gauge channel and the protection sleeve channel to drill a target portion of bone, wherein the image sensor generates a plurality of successive images of the drill-bit surface to detect variations in the position of the drill-bit. In an embodiment, the depth gauge further comprises a clamping portion, the clamping portion including a plurality of adjustable arms configured to clamp the depth gauge to the protection sleeve. In another embodiment, the depth gauge further comprises a rotatable clamp adjustment mechanism, wherein rotating the adjustment mechanism in a first direction moves the plurality of arms toward a central longitudinal axis of the depth gauge and rotating the adjustment mechanism in a second direction moves the plurality of arms away from the central longitudinal axis. In another embodiment, the system further comprises a processing unit coupled to the image sensor, the processing unit comparing the movement of identifiable points within the plurality of successive images to calculate the distance the drill-bit moves through the depth gauge channel. In a further embodiment, the depth gauge further comprises a display screen coupled to the processing unit, the display screen displaying the distance the drill-bit moves through the channel.

The present disclosure also relates to a method for measuring the depth of a hole comprising positioning a depth gauge on a protection sleeve, the depth gauge comprising a body extending a central longitudinal axis and including a channel and a light-passing hole, the light-passing hole open to the channel, a light source mounted in the body, an image sensor mounted in the body, and a clamp coupled to the body, the clamp including a plurality of adjustable arms configured to clamp the device to a protection sleeve, inserting a drill-bit through the channel and the protection sleeve, passing a first light beam generated by the light source through the light-passing hole toward a surface of the drill-bit extending through the channel, the first light beam forming an incident light beam when reflected from the drill-bit surface and generating a plurality of successive images of the drill-bit surface, via the image sensor, to detect variations in the position of the drill-bit moving through the channel. In an embodiment, the depth gauge further comprises a rotatable clamp adjustment mechanism, wherein rotating the adjustment mechanism in a first direction moves the plurality of arms toward the central longitudinal axis and rotating the adjustment mechanism in a second direction moves the plurality of arms away from the central longitudinal axis. In another embodiment, the method further includes comparing, via processing unit coupled to the image sensor, the movement of identifiable points within the plurality of successive images to calculate the distance the drill-bit moves through the channel. In an embodiment, the light source is an infrared laser source. In a further embodiment, the method comprises displaying the distance the drill-bit moves through the channel on a display screen coupled to the processing unit. In another embodiment, the method includes tracking the relative change in linear acceleration, via the processing unit, to identify when the drill-bit has exited a second cortex of the target bone. In a further embodiment, the method includes providing an indication signal to the user when the drill-bit is exiting the second cortex.

BRIEF DESCRIPTION

DETAILED DESCRIPTION

Figure 1:
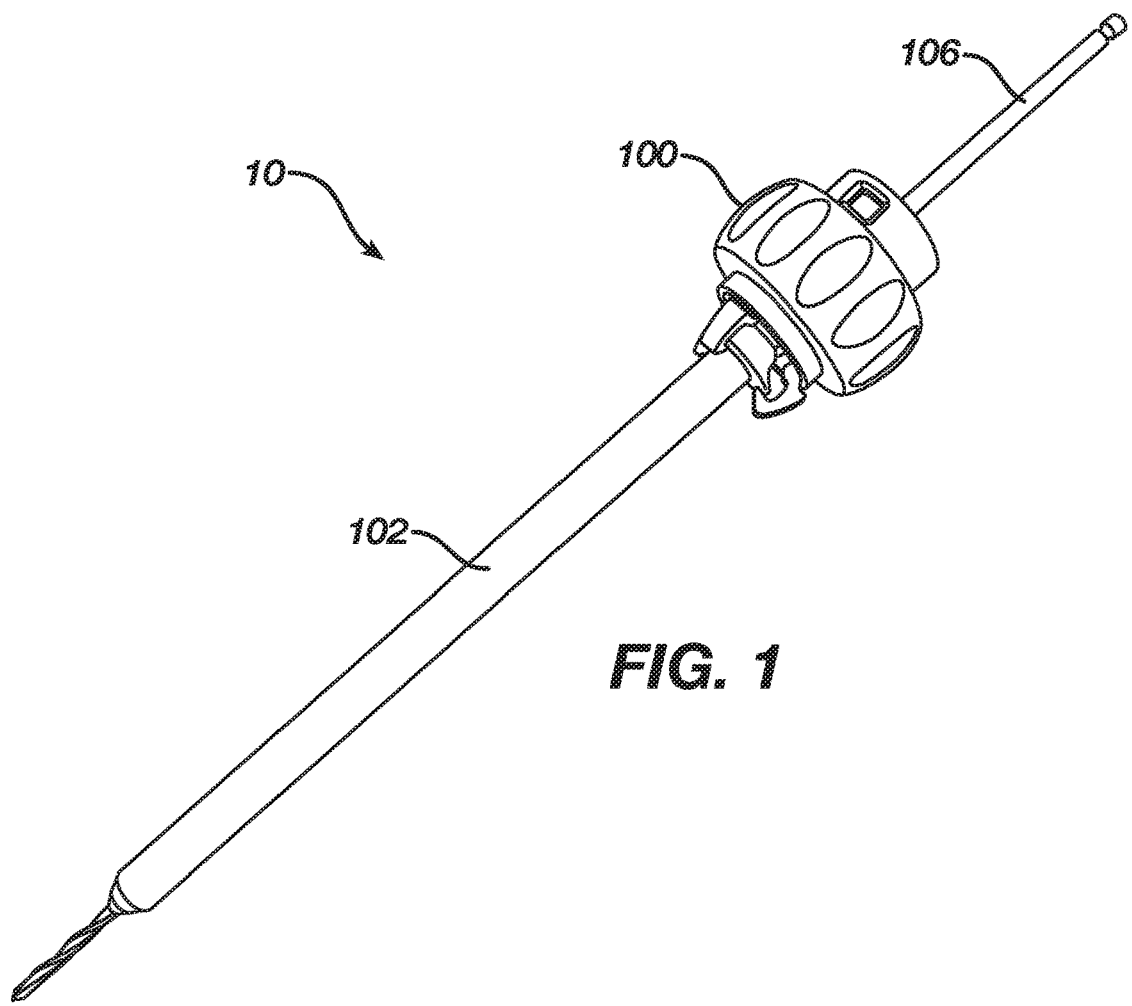
FIG. 1 shows a side view of a depth gauge system according to an exemplary embodiment of the present disclosure.

The present disclosure may be understood with reference to the following description and the appended drawings, wherein like elements are referred to with the same reference numerals. The present disclosure relates to a method and device for measuring the required length of a bone screw using an infrared laser diode. In an exemplary embodiment, the measuring device includes an adjustable universal clamp interface for mounting the device on a drill sleeve or soft tissue protection sleeve. Those skilled in the art will appreciate that the principles of the invention apply to any distance measurement that may be necessary in a patient during a surgical procedure. It should be noted that the terms "proximal" and "distal" as used herein are intended to refer to a direction toward (proximal) and away from (distal) a user of the device.

Figure 2:
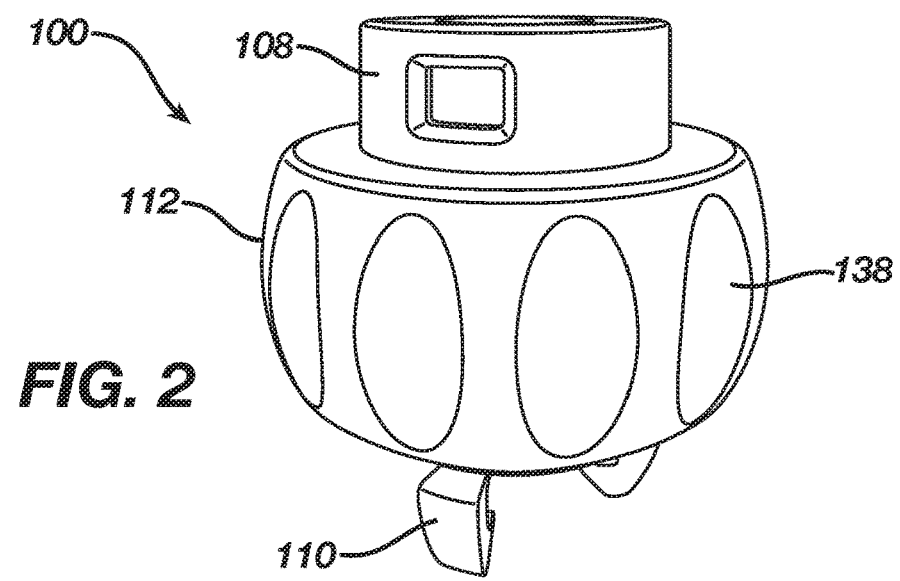
FIG. 2 shows a side view of the depth gauge of the system of FIG. 1 according to an exemplary embodiment.
Figure 3:
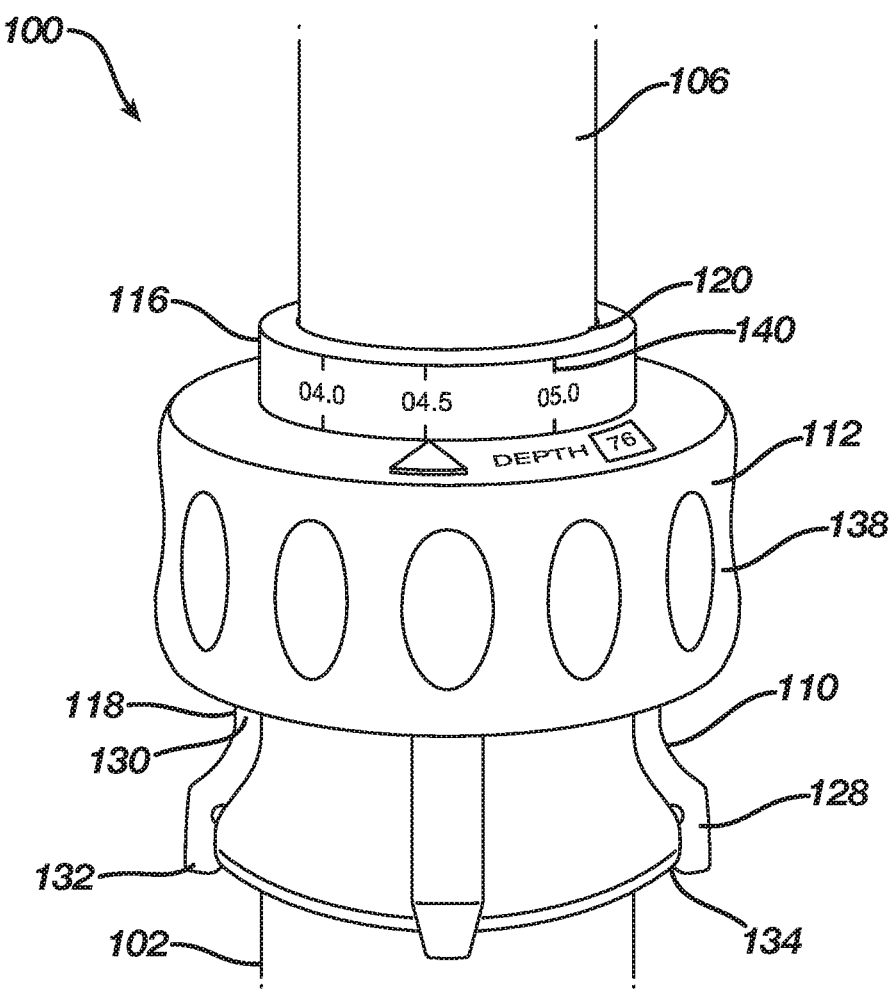
FIG. 3 shows a perspective view of the depth gauge of the system of FIG. 1.
Figure 4:
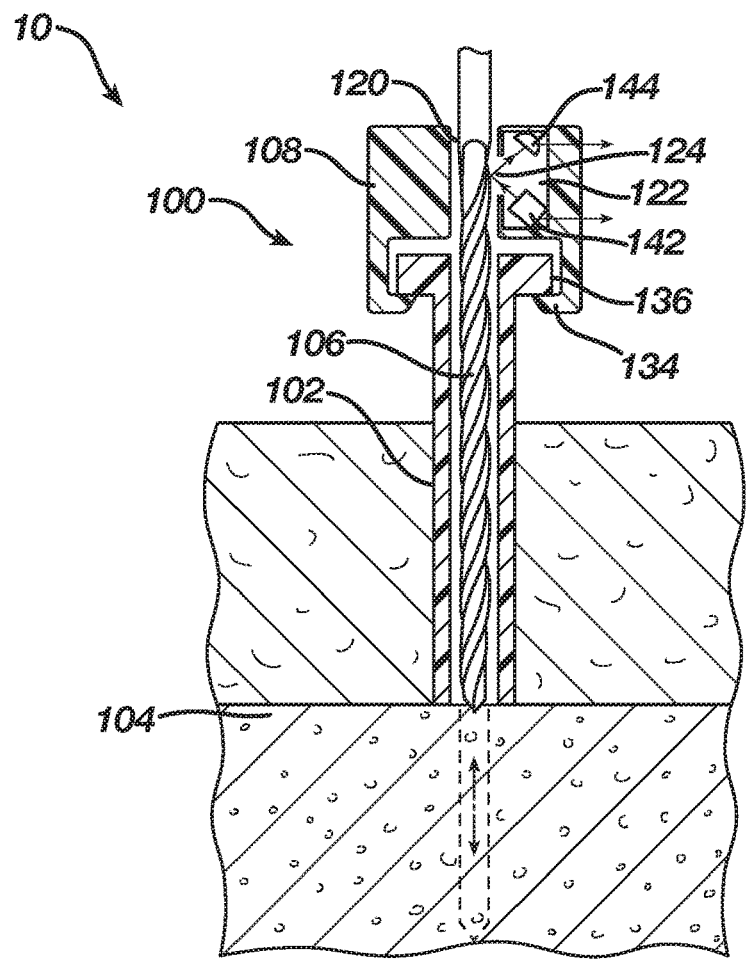
FIG. 4 shows a cross-sectional view of the system of FIG. 1.

FIG. 1 illustrates an exemplary depth measuring system 10 including a depth gauge device 100 positioned on a protection sleeve 102 during a surgical procedure to measure drill-bit linear movement (depth) through a bone 104 within the patient's body. For example, during an operation, the device 100 may be used to measure the movement of a drill-bit 106 extending through the depth gauge device 100 and the protection sleeve 102. The depth gauge device 100, as shown in FIGS. 2-4, includes a depth gauge body 108, an adjustable clamp 110 with a clamp adjustment mechanism 112 and an infrared (IR) laser imaging system 114. The body 108 extends from a proximal end 116 to a distal end 118 and includes a channel 120 extending therethrough. In this embodiment, the channel 120 is substantially cylindrical in shape and adapted for insertion of the drill-bit 106 therethrough. However, it will be understood that the channel 120 may be any shape suitable for insertion of a drill-bit 106. The body 108 includes, in this embodiment, a mounting portion 122 open to the channel 120 for mounting of the IR laser imaging system 114. The mounting portion 122 may be, for example, a hollowed space within the body 108. In another embodiment, the channel 120 may include a lateral cutout (not shown) within the wall of the channel 120 into the body 108 so that the IR imaging system 114 may be mounted within the cutout without protruding into the channel 120 or coming into contact with the drill-bit 106. In the present embodiment, the mounting portion 122 is open to the channel 120 via a light-passing hole 124 in the channel 120 wall. The light-passing hole 124 is sized and shaped for the passing of a first light beam 148 from the light source 142 within the mounting portion 122 and a second incident light beam 154 reflected off of the surface 150 of the drill-bit 106 to the image sensor 144 (as discussed in further detail below). The light-passing hole 124 protects the light source 142 from detecting any outside light other than the second incident light beam 154.

In an exemplary embodiment, the depth gauge body 108 includes an adjustable universal clamp 110, including an adjustment mechanism 112, coupled to the distal end 118. The clamp 110 may include a plurality of arms 128 extending from a proximal end 130 coupled to the body 108 to a free distal end 132 adapted for clamping the device 100 to the protection sleeve 102, as can be seen in FIGS. 3-4. The proximal ends 130 of the clamp arms 128 are distributed about a circumference of the distal end of the body 108 to provide stable engagement between the device 100 and the protection sleeve 102. In an embodiment, the distal ends 132 of the arms 128 include a hook feature 134 to hook about a head 136 of the protection sleeve 102. However, it will be understood that the distal ends 132 may be shaped in any way that provides a stable clamp connection between the device 100 and the protection sleeve 102. The arms 128 may be tightened about the protection sleeve 102 via rotation of the clamp adjustment mechanism 112. The clamp adjustment mechanism 112 comprises a rotating member 138 coupled to the arms 128 for adjustment thereof. For example, in this embodiment rotation of the rotating member 138 in a first direction moves the arms 120 inwardly toward the central longitudinal axis, L, of the device 100 while rotation of the rotating member 138 in a second opposing direction moves the arms 128 outwardly away from the longitudinal axis. Thus, the clamp 110 can be adjusted to size of the protection sleeve 102 to which it is being coupled. In this embodiment, the clamp adjustment mechanism 112 is disposed about the outer circumference of the body 108. However, it will be understood that the adjustment mechanism 112 may be positioned anywhere on the body 108 so long as rotation of the adjustment mechanism 112 facilitates movement of the arms 128 as described. As shown in FIG. 3, the adjustment mechanism 112 may include markings 140 indicating a protection sleeve diameter around which the clamp 110 will fit when the adjustment mechanism 112 is aligned with a specified marking 140. As shown, in this embodiment, the body 102 includes markings 140 numbered at 0.5 intervals (indicating the size of the drill bit to be used), but any type of marking at any interval indicating the varying sizes is sufficient.

Figure 5:
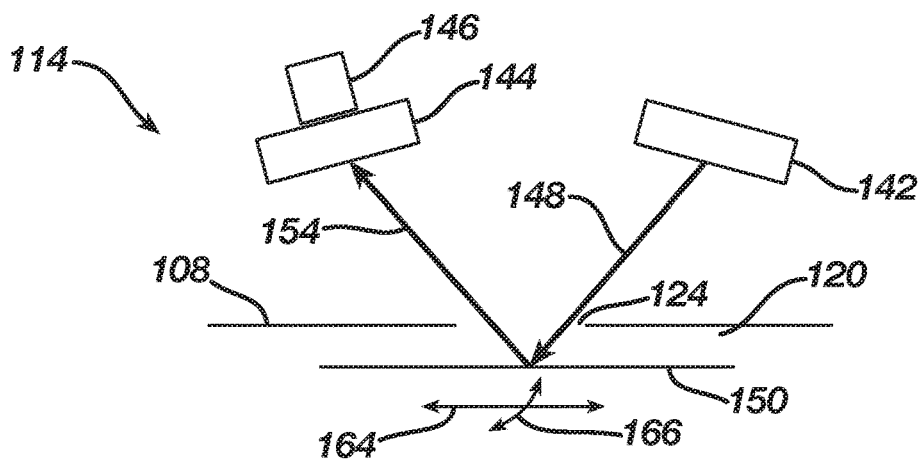
FIG. 5 shows the path of an infrared light beam emitted by the light source of the system of FIG. 1 according to an exemplary embodiment.

The IR laser imaging system 114, as shown in FIGS. 4-5, is mounted within the mounting portion 122 of the body 108. The imaging system 114 uses digital image correlation to determine relative position between the device 100 and the drill-bit 106, which may be in motion (as represented by arrows 164, 166) in any direction in a two-dimensional plane relative to the device 100. The imaging system 114 includes a light source 142, an image sensor 144 and a processing unit 146 all of which are, in this embodiment, mounted inside the body 108. In an exemplary embodiment, the light source 142 provides an infrared (IR) laser beam 148 to increase the resolution of images taken by the image sensor 144 and thus, more accurately measure the depth of holes drilled. In the present embodiment, an IR laser beam 148 is directed linearly from the light source 142 through the light-passing hole 124 directly to the surface 150 of the drill-bit 106 and a surface image 152 is then generated from the incident light 154 reflected from the drill-bit surface 150. However, it will be understood by those skilled in the art that the IR imaging system 114 may include one or more interfaces (not shown) to reflect and direct the IR laser beam 148 along a specified path to or from the drill-bit surface 150 so long as the incident light reflected by the drill-bit surface 150 generates a surface image. In this embodiment, the IR laser beam 148 travels at an incident angle of, for example, about 45 degrees from the light source 142. However, any incident angle may be used to direct the IR laser beam 148 to the drill-bit surface 150. The light source 142 may be any infrared laser, such as an infrared laser diode, emitting an infrared light beam.

The image sensor 144 is also mounted in the mounting portion 122 and includes image sensing cells (not shown) facing the drill-bit surface 150 for sensing the reflected incident laser beam 154 from the drill-bit surface 150 and generating a detected image 152. As would be understood by those skilled in the art, existing sensors are capable of taking more than 12,000 frames per second (fps), with a resolution up to 12,000 dots per inch (dpi) and may sense acceleration of up to 40G, and speeds up to 7 meters per second (m/s). In the present embodiment, the image sensor captures up to 12000 successive frames or more per second. The image sensor 144 images the naturally occurring texture in the material of the drill-bit 106 so that no gradations or markings are necessary on the drill bit 106.

Figure 6:
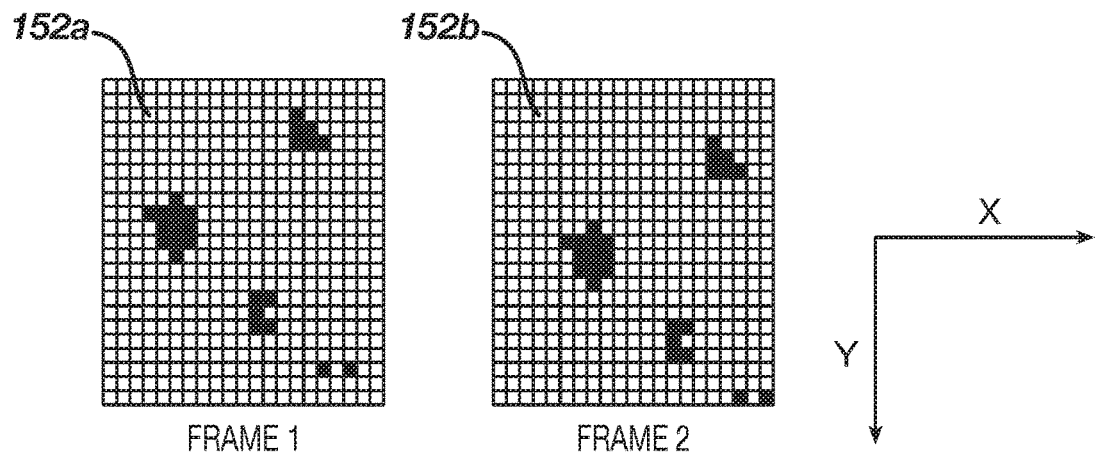
FIG. 6 shows two exemplary frames captured by an image sensor of the system of FIG. 1 according to an exemplary embodiment.

The processing unit 146 is coupled to the image sensor 144 to generate electrical signals from the detected images 152 generated by the image sensor 144. Specifically, in this embodiment, the image sensor 144 takes successive images of the drill-bit surface 150. This surface 150, when lit at a grazing angle by the light source 142, casts distinct shadows that resemble hilly terrain. Images 152 of these surface features are captured in succession and compared to each other to determine an amount of movement of the drill bit represented by the differences between successive images. The processing unit 146 processes these images 152 using cross correlation to calculate an offset between successive image in both the x-direction and the y-directions. For example, the processing unit 146 may detect drill-bit axial translation as well as rotational motion. By comparing successive stored images 152a, 152b, as represented in FIG. 6, relative motion can be determined such that a correlation calculation of the patterns within the images 152a, 152b can be used to determine the distance and direction of the movement represented by the difference between the successive images. For example, a first captured image overlaps partially with a prior captured imaged so that a single portion of the drill bit is represented in both images. Thus, software algorithms of the processing unit 146 may look, for example, at specific identifiable points in each image 152 and then calculate the distance and direction of the relative movement by noting the movement of such identifiable points. Depending on how fast the drill-bit 106 is moving, each image 152a, 152b may be offset from the previous one by a fraction of a pixel or as many as several pixels. By storing successive image pairs, these characteristics that "overlap" can be identified, yielding direction and magnitude of translation in both the x-direction and the y-direction. In the present embodiment, the detected rotational movement of the drill-bit 106 is discarded and only linear translation up and down (y-direction) is recorded by the processing unit 146. However, in another embodiment, the rotational movement (x-direction) of the drill-bit 106 may also be stored for informational purposes. In an embodiment, the processing unit 146 may be coupled to a display screen 156 located on the device 100 for displaying the recorded linear movement (depth). In an exemplary embodiment, the processing unit 146 includes network communication capabilities such as Wi-Fi or Bluetooth through which the device 100 may be connected to, for example, a computer device or a power-driven drilling tool (for example to trigger the power-tool off when passing the second cortex).

Figure 7:
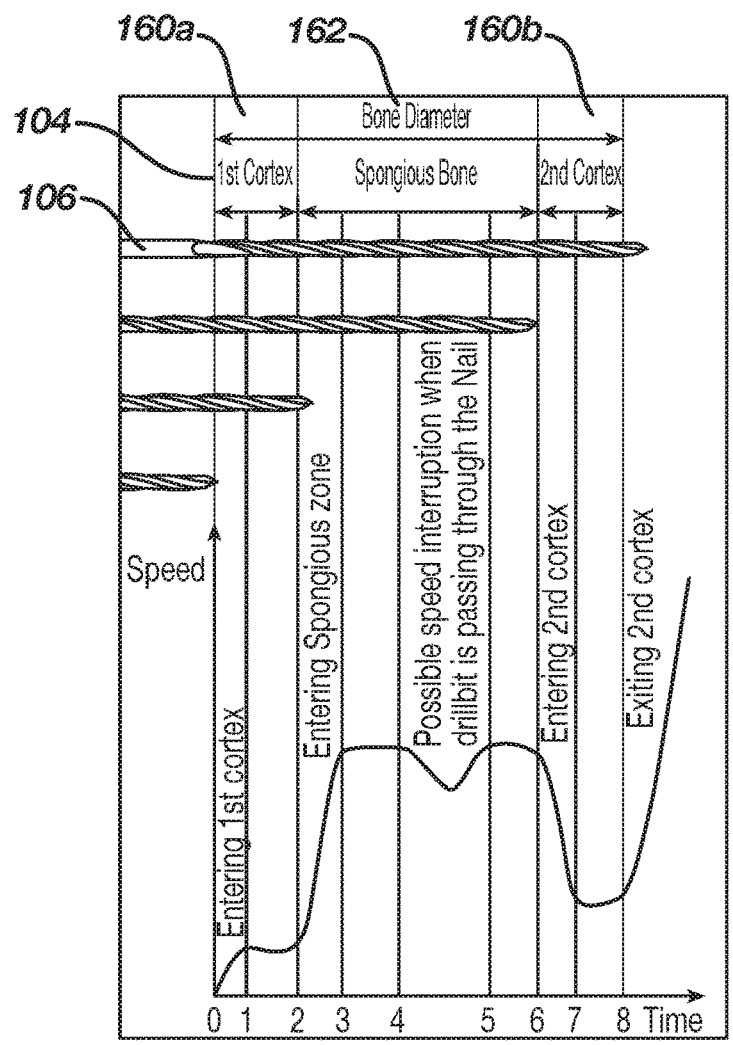
FIG. 7 shows a graph of the acceleration pattern of a drill of the system of FIG. 1 passing through a long bone.

In an embodiment, the device software may recognize the acceleration or deceleration patterns of the drill-bit to indicate what portion of the bone the drill-bit 106 is passing through. For example, as can be seen in FIG. 7, a typical long bone 10 (i.e., femur or tibia) includes a hard outer-layer, cortical bone 160a, 160b (zones 1 and 3), and a softer inner core of spongious bone 162 (zone 2). A drill bit entering the spongious core 162 will accelerate from its speed in the harder first cortex 160a, as shown in the graph of FIG. 7. Contrarily, the drill-bit 106 will decelerate when entering the second cortex 160b of the bone from the spongious core 162. The device software according to this embodiment detects and tracks these changes in linear acceleration to recognize and indicate to the user when the drill-bit 106 is passing from one portion of bone to another (e.g., exiting the spongious core 162 and entering the second cortex (zone 2) 160b (zone 3)). The indicator may be either audio or visual. For example, in an embodiment, the device 100 may provide an audible beep or ping when the drill-bit 106 is exiting the second cortex 106b. In another embodiment, the device 100 may provide a visible blinking light when the drill-bit 106 is exiting the second cortex 106b. This indication signal may prevent unnecessary drilling past the second cortex 106b and thus, prevent unnecessary trauma to surrounding tissue.

In use, the depth gauge device 100 is attached to the proximal end of a protection sleeve 102. The clamp arms 128 are sized to the diameter of the protection sleeve head 136 by rotation of the adjustment mechanism 112. When the device 100 is attached to the protection sleeve 102, both the device 100 and the protection sleeve 102 are held stationary relative to one another and the target bone 104. The drill-bit 106 may then be inserted through the central channel 120 and the channel of the protection sleeve 102. When drilling begins, the light source 142 projects an IR laser beam 148 through the light-passing hole 124 and on to the drill-bit surface 150. The incident light beam 154 reflected from the drill-bit surface 150 to the image sensor 144 is captured in successive image frames 152 which are processed by the processing unit 146 to calculate the linear motion of the drill-bit 106 relative to the depth gauge device 100. The linear movement may be displayed to the user on a display screen 156 or otherwise communicated to a user. In an embodiment, the linear movement is updated in real time. In another embodiment, the linear movement is provided after drilling has been completed.

It will be appreciated by those skilled in the art that changes may be made to the embodiments described above without departing from the inventive concept thereof. It should be further appreciated that structural features and method associated with one of the embodiments can be incorporated into other embodiments. It is understood, therefore, that this invention is not limited to the particular embodiments discloses, but rather modifications are also covered within the scope of the present invention as defined by the appended claims.

What is claimed is:

1. A depth gauge device, comprising:
   a body extending along a central longitudinal axis and including a channel and a light-passing hole, the light passing hole open to the channel;
   a protection sleeve having an enlarged head;
   a light source mounted in the body for generating a first light beam, the first light beam passing through the light-passing hole toward a surface of a drill-bit extending through the channel, the first light beam forming an incident light beam when reflected away from the drill-bit surface;
   an image sensor mounted in the body for sensing the incident light beam and generating a plurality of successive images of the drill-bit surface to detect variations in the position of the drill-bit moving through the channel; and
   a clamp coupled to the body, the clamp including a plurality of adjustable arms configured to clamp the body to the protection sleeve, the adjustable arms having hooks configured to engage the enlarged head.

2. The device of claim 1, wherein the clamp further comprises a rotatable clamp adjustment mechanism, wherein rotating the adjustment mechanism in a first direction moves the plurality of adjustable arms toward the central longitudinal axis and rotating the adjustment mechanism in a second direction moves the plurality of adjustable arms away from the central longitudinal axis.

3. The device of claim 1, further comprising a processing unit coupled to the image sensor, the processing unit comparing the movement of identifiable points within the plurality of successive images to calculate the distance the drill-bit moves through the channel.

4. The device of claim 3, further comprising a display screen coupled to the processing unit, the display screen displaying the distance the drill-bit moves through the channel.

5. The device of claim 3, wherein the processing unit includes Bluetooth capabilities.

6. The device of claim 1, wherein the light source is an infrared laser source.

7. The device of claim 1, wherein the light-passing hole is sized and shaped for the passing of the first light beam from the light source and the incident light beam reflected from the drill-bit surface.

8. The device of claim 1, wherein when the device is clamped to the protection sleeve, the channel is aligned with a channel extending through the protection sleeve.

9. A system for measuring the depth of a hole, comprising:
   a depth gauge device according to claim 1; and
   a drill-bit configured to extend into the channel of the body of the depth gauge and a channel in the protection sleeve to drill a target portion of a bone,
   wherein:
   when the body is clamped to the protection sleeve, the channel in the protection sleeve is aligned with the channel of the body of the depth gauge,
   the image sensor generates a plurality of successive images of the drill-bit surface to detect variations in the position of the drill-bit, and
   the adjustable arms clamp the depth gauge to the enlarged head of the protection sleeve.

10. A method for measuring the depth of a hole, comprising:
    inserting a drill-bit into a depth gauge device according to claim 1, wherein the drill bit passes through the channel of the body and through the protection sleeve, wherein the hooks on the adjustable arms engage the enlarged head of the protection sleeve;
    passing a first light beam generated by the light source through the light-passing hole toward a surface of the drill-bit extending through the channel, the first light beam forming an incident light beam when reflected from the drill-bit surface; and
    generating a plurality of successive images of the drill-bit surface, via the image sensor, to detect variations in the position of the drill-bit moving through the channel.

11. The method of claim 10, wherein the depth gauge device further comprises a rotatable clamp adjustment mechanism, wherein rotating the adjustment mechanism in a first direction moves the plurality of adjustable arms toward the central longitudinal axis and rotating the adjustment mechanism in a second direction moves the plurality of arms away from the central longitudinal axis.

12. The method of claim 10, further comprising comparing, via a processing unit coupled to the image sensor, the movement of identifiable points within the plurality of successive images to calculate the distance the drill-bit moves through the channel.

13. The method of claim 12, further comprising displaying the distance the drill-bit moves through the channel on a display screen coupled to the processing unit.

14. The method of claim 10, wherein the light source is an infrared laser source.

15. The method of claim 10, further comprising tracking the relative change in linear acceleration, via a processing unit, to identify when the drill-bit has exited a second cortex of the target bone.

16. The method of claim 15, further comprising providing an indication signal to the user when the drill-bit is exiting the second cortex.

* * * * *